(12) United States Patent
McCallie et al.

(10) Patent No.: US 8,019,623 B2
(45) Date of Patent: Sep. 13, 2011

(54) SYSTEM AND METHODS FOR PROVIDING MEDICATION SELECTION GUIDANCE

(75) Inventors: David McCallie, Stilwell, KS (US); Christopher Finn, Liberty, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

(21) Appl. No.: 12/650,515

(22) Filed: Dec. 30, 2009

(65) Prior Publication Data

US 2010/0106529 A1 Apr. 29, 2010

Related U.S. Application Data

(62) Division of application No. 11/319,797, filed on Dec. 28, 2005.

(60) Provisional application No. 60/640,028, filed on Dec. 29, 2004.

(51) Int. Cl.
*G06Q 10/00* (2006.01)
*G06Q 50/00* (2006.01)

(52) U.S. Cl. .......................................................... 705/2

(58) Field of Classification Search ................... 705/2, 3
See application file for complete search history.

(56) References Cited

U.S. PATENT DOCUMENTS

| | | |
|---|---|---|
| 2002/0010597 A1 | 1/2002 | Mayer et al. |
| 2002/0032581 A1 | 3/2002 | Reitberg |
| 2002/0042726 A1 | 4/2002 | Mayaud |
| 2002/0095316 A1* | 7/2002 | Toan et al. .................... 705/4 |
| 2002/0128866 A1* | 9/2002 | Goetzke et al. ................ 705/2 |
| 2002/0147617 A1* | 10/2002 | Schoenbaum et al. .......... 705/4 |
| 2003/0050802 A1* | 3/2003 | Jay et al. ....................... 705/3 |
| 2004/0006490 A1* | 1/2004 | Gingrich et al. ............... 705/2 |
| 2004/0072457 A1 | 4/2004 | Kalies |
| 2005/0261939 A1 | 11/2005 | Augspurger et al. |
| 2005/0261941 A1 | 11/2005 | Scarlat |

OTHER PUBLICATIONS

Non Final Office Action of U.S. Appl. No. 11/319,797, dated Jan. 22, 2010.

* cited by examiner

*Primary Examiner* — Gerald J. O'Connor
*Assistant Examiner* — Trang Nguyen
(74) *Attorney, Agent, or Firm* — Shook Hardy & Bacon LLP (57) ABSTRACT

A system and associated methods provide medication selection guidance at the time of a prescription event for a given patient, or at other times, such as when changes occur in the patient's healthcare plan coverage. In one medication selection guidance method, information is received regarding a clinician-preferred medication prescription related to a selected patient, and based on at least one record of the selected patient, a specific information set is retrieved. For instance, the specific information set may include medications the patient is currently taken, healthcare plan coverage for the patient, or other types of information. Then, other medications that can be prescribed to the patient as alternatives to the clinician-preferred medication prescription may be determined based on the specific information set. These alternative medications may be evaluated against the patient's healthcare plan coverage to present available medication options and associated out-of-pocket costs to the patient.

7 Claims, 6 Drawing Sheets

FIG. 6

SYSTEM AND METHODS FOR PROVIDING MEDICATION SELECTION GUIDANCE

CROSS-REFERENCE TO RELATED APPLICATIONS

This application is a divisional of U.S. patent application Ser. No. 11/319,797 filed Dec. 28, 2005, entitled "System and Methods for Providing Medication Selection Guidance" and claims priority to commonly owned U.S. Provisional Application Ser. No. 60/640,028, filed Dec. 29, 2004, of which each application is assigned or under obligation of assignment to the same entity application and both of which are incorporated in this application by reference.

STATEMENT REGARDING FEDERALLY SPONSORED RESEARCH OR DEVELOPMENT

Not Applicable.

BACKGROUND

The present invention relates generally to the field of computer software. More particularly, the present invention relates to a computerized system and methods for providing guidance of medication selection.

Clinicians have traditionally made decisions regarding which medication to prescribe for a patient's health condition or illness based on medication information that they have memorized or can quickly look up in a reference guide. The clinician may have learned about a given kind of medication (as an example, a specific anti-inflammatory) from a medical journal, advertisement, educational lecture, or other means. However, clinicians rarely have the time or resources to compare a specific medication with all other medications that provide a similar therapeutic effect and have an acceptable level of efficacy. It may be that medications other than the medication chosen by the clinician can provide the therapeutic benefit that the clinician had intended while better meeting a particular patient's needs. For instance, the chosen medication may not be covered by the patient's healthcare insurance plan, or may otherwise require a high out-of-pocket cost to the patient as compared to other medications that could provide the same therapeutic effect for the patient. The clinician's chosen medication may also have other disadvantages that make proper compliance with the prescription administering difficult. As one example, the chosen medication may have to be dispensed to a patient multiple times a day, whereas a patient would prefer a once-a-day dose. The chosen medication may also be documented to have caused unwanted side effects in a large segment of the population that have taken the medication. In these situations, other medications may be more appropriate to address the specific health condition of the patient.

A solution is needed for providing additional options and guidance in medication selection for a patient that is more tailored to the needs of the particular patient.

BRIEF SUMMARY

A system and associated methods provide medication selection guidance at the time of a prescription event for a given patient, or at other times, such as when changes occur in the patient's healthcare plan coverage. In one aspect of the invention, a medication selection guidance method for a prescribing event is employed. According to this method, information is received regarding a clinician-preferred medication prescription related to a selected patient, and based on at least one record of the selected patient, a specific information set is retrieved. For instance, the specific information set may include medications the patient is currently taken, healthcare plan coverage for the patient, or other types of information. Then, other medications that can be prescribed to the patient as alternatives to the clinician-preferred medication prescription may be determined based on the specific information set. Optionally, an evaluation may be conducted for the alternative medications against the patient's healthcare plan coverage to present available medication options and associated out-of-pocket costs to the patient in a report.

Another aspect of the invention includes a method that provides guidance in the selection of medication for a patient. According to the method, information is receive regarding at least one first medication, and based on at least one record of the selected patient, a specific information set is retrieved that includes healthcare plan formulary coverage information for the patient associated with a pricing schedule. Then, therapeutic equivalent medications to the at least one first medication are determined based on the healthcare plan formulary coverage information. The therapeutic equivalent medications include medications that can be administered to the patient as alternatives to the at least one first medication and which are included in the healthcare plan formulary coverage information. The therapeutic equivalent medications may be displayed along with information regarding how the therapeutic equivalent medications fit into the associated pricing schedule of the healthcare plan formulary coverage information.

In still another aspect of the invention, a method is employed for providing guidance in the selection of medication for a patient. According to the method, information is received regarding a prescribing event surrounding at least one first medication, and based on at least one record of the selected patient, a specific information set is retrieved that includes medications the specific patient is currently taking. A drug-drug interaction analysis is performed based on the at least one first medication and current medications taken by the specific patient. If a drug-drug interaction match is found between the at least one first medication and any of the currently taken medications, then medications are located that would be therapeutic equivalent medications to at least one of the currently taken medications and the at least one first medication involved in the match.

Provided in another aspect of the invention is a method for auditing patient medication costs in response to changes in healthcare plan coverage for the patient. According to the method, information is received regarding changes in the healthcare plan of the patient. More specifically, the information involves a medication formulary coverage scheme of the healthcare plan. Based on at least one record of the patient, a specific information set is retrieved that includes medications the patient is currently taking. Finally, based at least on the information received regarding a change in the healthcare plan of the patient, the cost for medications the patient is currently taking is determined utilizing the healthcare plan medication formulary coverage scheme.

BRIEF DESCRIPTION OF THE SEVERAL VIEWS OF THE DRAWING

In the accompanying drawings which form a part of the specification and are to be read in conjunction therewith and in which like reference numerals are used to indicate like elements in the various views.

DETAILED DESCRIPTION

Systems and methods of the present invention provide improved efficiencies in guiding medication selection for a given patient by a clinician. For instance, various embodiments are provided for determining patient costs for various medication prescription options that may provide a desired therapeutic effect for the patient. Other embodiments facilitate the auditing of patient medication costs in response to changes in healthcare plan coverage for the patient. These and other features of the present invention may be further understood from the below description.

General Computing System Environment

Figure 1:
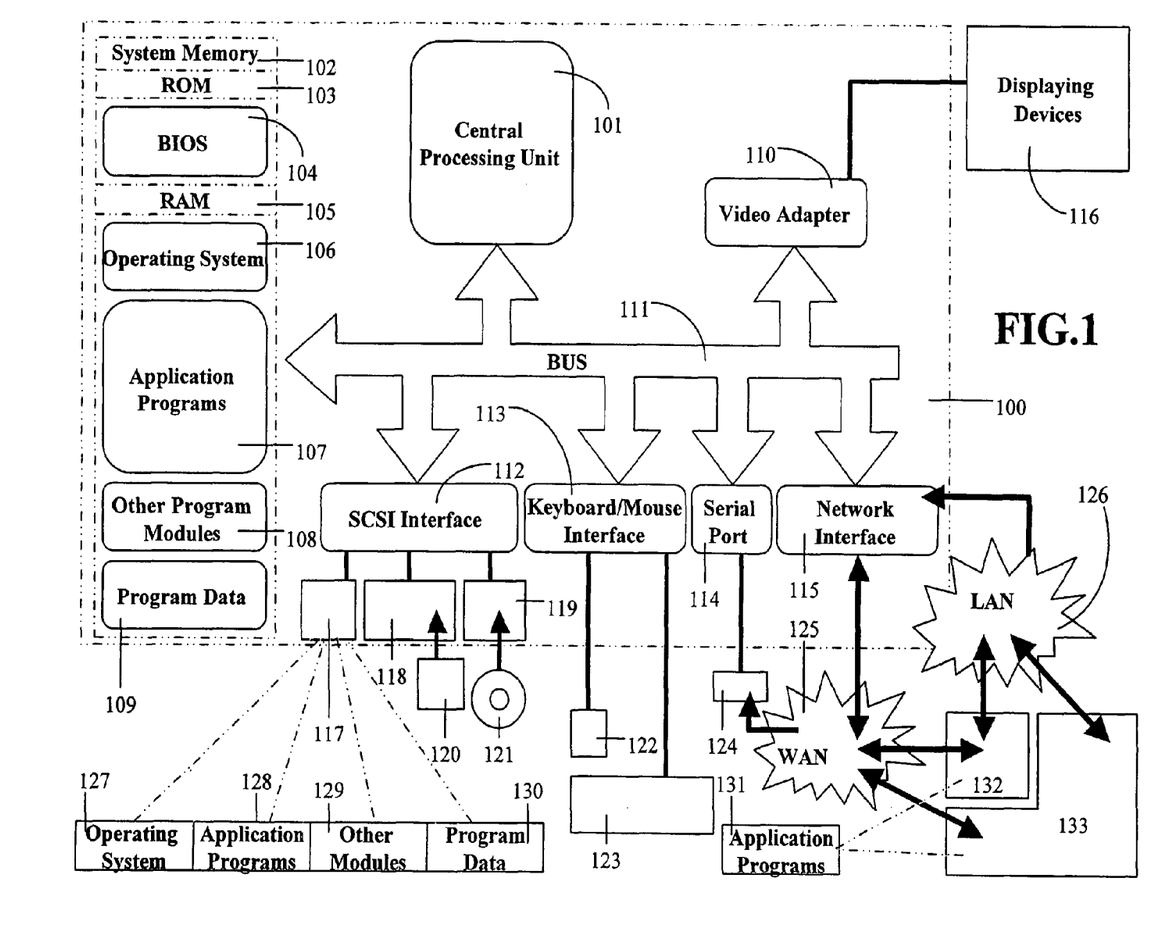
FIG. 1 is a block diagram of an exemplary computing system suitable for use in implementing the present invention.

FIG. 1 illustrates an example of a suitable computing system environment in which the invention may be implemented. The computing system environment is only one example of a suitable computing environment and is not intended to suggest any limitation as to the scope of use or functionality of the invention. Neither should the computing system environment be interpreted as having any dependency or requirement to any one or combination of components illustrated in the exemplary operating environment.

The present invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, cellular telephones, portable wireless devices, multiprocessor systems, microprocessor-based systems, programmable consumer electronics, network PCs, minicomputers, mainframe computers, distributed computing environments that include any of the above systems or devices, and the like.

The present invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 1, an exemplary system for implementing the invention includes a general purpose computing device in the form of a computer system 100. System 100 serves at least in part as a general medical information system. Components of system 100 include, but are not limited to, a processing unit 101, a system memory 102, and a system bus 111 that couples various system components including the system memory 102 to the processing unit 101. The system bus 111 may be any of several types of bus structures including a memory bus or memory controller, a peripheral bus and a local bus using any of a variety of bus architecture. By way of example, and not limitation, such architectures include Industry Standard Architecture (ISA) bus, Micro Channel Architecture (MCA) bus, Enhanced ISA (EISA) bus, Video Electronics Standard Association (VESA) local bus, and Peripheral Component Interconnect (PCI) bus also known as Mezzanine bus.

System 100 typically includes a variety of computer readable media. Computer readable media can be any available media that can be accessed by system 100 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is mot limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by system 100. Communications media typically embodies computer readable instructions, data structures, program modules or other data in a modulated data signal such as a carrier wave or other transport mechanism and includes any information delivery media. The term "modulated data signal" means a signal that has on or more of its characteristics set or changed in such a manner as to encode information in the signal. By way of example, and not limitation, communication media includes wired media such as a wired network or direct wired connection, and wireless media such as acoustic, radio frequency (RF), infrared and other wireless media. Combinations of any of the above should also be included within the scope of computer readable media.

The system memory 102 includes computer storage media in the form of a volatile and/or nonvolatile memory such as read only memory (ROM) 103 and random access memory (RAM) 105. A basic input/output system (BIOS) 104, containing the basic routines that help to transfer information between elements within system 100, such as during start-up, s typically stored in ROM 103. RAM 105 typically contains data and/or program modules that are immediately accessible to and/or presently being operated on by processing unit 101. By way of example, and not limitation, FIG. 1 illustrates operating system 106, application programs 107, other program modules 108, and program data 109.

The system 100 may also include other removable/nonremovable, volatile/nonvolatile computer storage media. By way of example only, FIG. 1 illustrates a hard disk drive 117 that reads from or writes to nonremovable, nonvolatile magnetic media, a magnetic disk drive 118 that reads from or writes to removable, nonvolatile magnetic disk 120, and an optical disk drive 119 that reads from or writes to a removable, nonvolatile optical disk 121 such as a CD-ROM, DVD- ROM or other optical media. Other removable/nonremovable, volatile/nonvolatile computer storage media that can be used in the exemplary operating environment include, but are not limited to, magnetic tape cassettes, flash memory cards, digital video disks, digital video tape, Bernoulli cartridges, solid state RAM, solid state ROM, and the like. The hard disk drive 117, magnetic disk drive 118 and optical disk drive 119 are typically connected to the system bus 111 by a Small Computer System Interface (SCSI) 112. Alternatively, the hard disk drive 117, magnetic disk drive 118 and optical disk drive 119 may be connected to the system bus 111 by a hard disk drive interface, a magnetic disk drive interface, and an optical drive interface, respectively.

The drives and their associated computer storage media discussed above and illustrated in FIG. 1, provide storage of computer readable instructions, data structures, program modules and other data for the system 100. In FIG. 1, for example, hard disk drive 117 is illustrated as storing operating system 127, application programs 128, other program modules 129, and program data 130. Note that these components can either be the same as or different from operating system 106, application programs 107, other program modules 108, and program data 109. A user may enter commands and information into the system 100 through input devices such as a keyboard 123 and pointing device 122, commonly referred to as a mouse, trackball or touch pad. Other input devices (not shown) may include a microphone, joystick, game pad, satellite dish, scanner, or the like. These and other input devices are often connected to the processing unit 101 through a user input interface 113 or a serial port interface 114 that is coupled to the system bus 111, but may be connected by other interface and bus structures, such as a parallel port, game port or a universal serial bus (USB). A monitor 116 or other type of display device is also connected to the system bus 111 via an interface, such as a video adapter 110. In addition to the monitor 116, computers may also include other peripheral output devices such as speakers and printers, which may be connected through an output peripheral interface.

The system 100 may operate in a networked environment using logical connections to one or more remote computers, such as a remote computer 133 and/or other electronic devices, such as a communication device 132. The remote computer 133 may be a personal computer, a server, a router, a network PC, a peer device or other common network node, and typically includes many or all of the elements described above relative to the system 100, although only a memory storage device has been illustrated in FIG. 1. Remote computer 133 may, for example, be found at a variety of health system related locations, such as hospitals, other inpatient settings, pharmacies, a clinician's office/practice, ambulatory settings, testing labs and a patient's home environment, though other locations may be chosen as well. The communication device 132 may be a mobile cellular phone, mobile text-pager or other portable communications device, and typically includes some of the elements described above relative to the system 100. The logical connections depicted in FIG. 1 include a local area network (LAN) 126 and a wide area network (WAN) 125, but may also include other networks. Such networking environments are commonplace in offices, enterprise-wide computer networks, intranets and the Internet.

When used in a LAN networking environment, the system 100 may be connected to the LAN 126 through a networking interface or adapter 115. When used in a WAN networking environment, the system 100 typically includes a modem 124 or other means for establishing communications over the WAN 125, such as the Internet. The modem 124, which may be internal or external, may be connected to the system bus 111 via the serial port interface 114 or other appropriate mechanism. In a networked environment, program modules depicted relative to the system 100, or portions thereof, may be stored in the remote storage device. By way of example, and not limitation, FIG. 1 illustrates remote application programs 131 as residing on memory devices 132 and 133. It will be appreciated that the network connections shown are exemplary and other means of establishing a communications link between the computers and/or portable communication devices may be used.

Although many other internal components of the system 100 are not shown, those of ordinary skill in the art will appreciate that such components and the interconnection are well known. Accordingly, additional details concerning the internal construction of the system 100 need not be disclosed in connection with the present invention.

Those skilled in the art will understand that program modules such as the operating system 106 and 127, application programs 107 and 128, and program data 109 and 130 are provided to the system 100 via one of its memory storage devices, which may include ROM 103, RAM 105, hard disk drive 117, magnetic disk drive 118 or optical disk drive 119. Preferably, the hard disk drive 117 is used to store program data 130 and 109, application programs 107 and 128, and operating system 106 and 127.

When the system 100 is turned on or reset, the BIOS 104, which is stored in the ROM 103 instructs the processing unit 101 to load the operating system from the hard disk drive 117 into the RAM 105. Once the operating system 127 is loaded in RAM 105, the processing unit 101 executes the operating system code and causes the visual elements associated with the user interface of the operating system 127 to be displayed on the monitor 116 or other display device. When an application program 107 and 128 is opened by a user, the program code and relevant data are read from the hard disk drive 117 and stored in RAM 105.

Medication Selection Guidance

Figure 2:
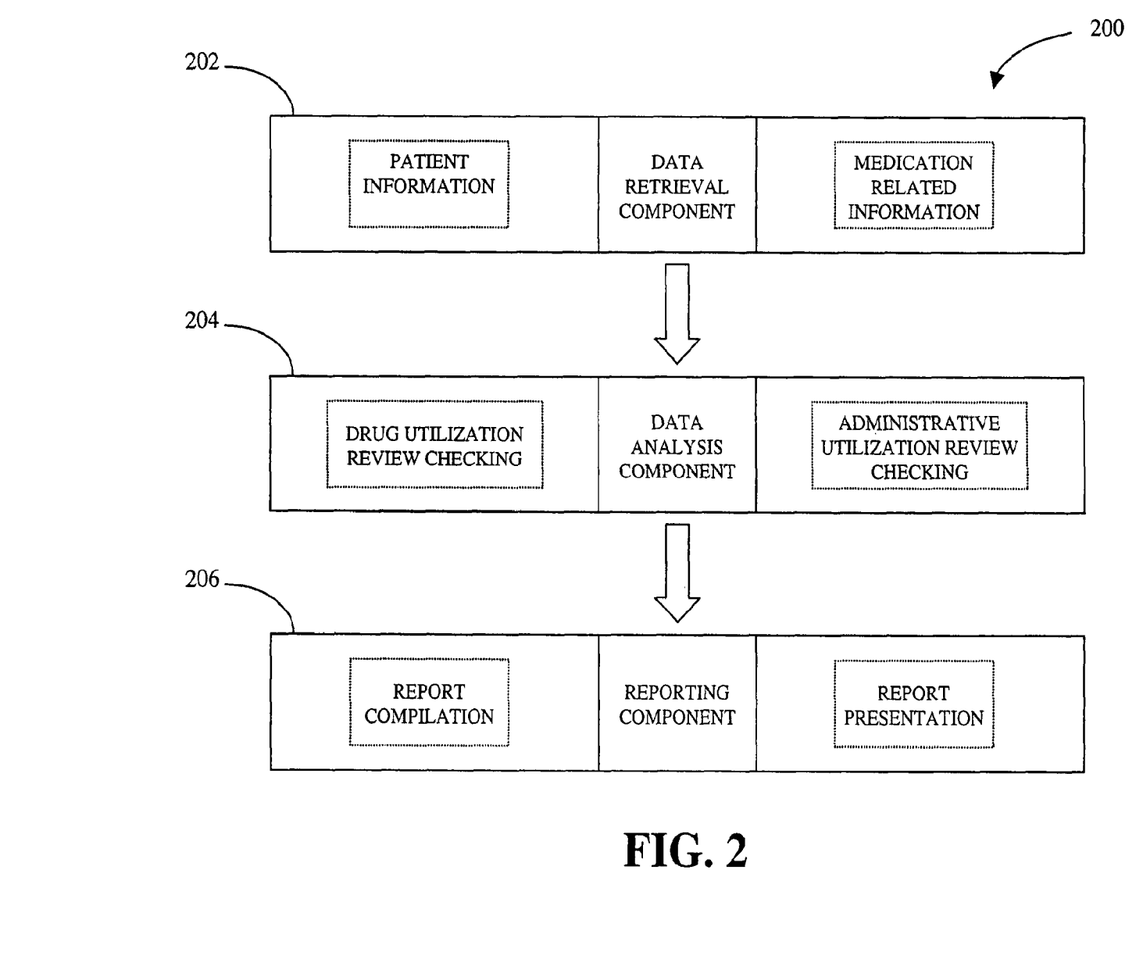
FIG. 2 is a block diagram of one embodiment of a set of component modules of the present invention illustrating the functional relationship between the modules.

Illustrated in FIG. 2 is the general flow of activity through a set of general component modules 200 functioning within the system 100. Through the utilization of the general component modules 200, guidance is provided in selecting, for a patient, medications that possess a desired therapeutic effect.

Various terminology discussed with respect to the present invention may have particular meaning as described below. For instance, the term "clinician" includes, but is not limited to, a treating physician, specialists such as surgeons, radiologists and cardiologists, emergency medical technicians, physician's assistants, nurse practitioners, nurses, physical therapists, pharmacists, dieticians, microbiologists, and the like, and aides or assistants thereto. The term "patient" refers to a person that is receiving or has received health-care-related services, including medication prescription services, in any location in a medical environment (e.g., hospitals or other inpatient or outpatient settings, a clinician's office/practice location, ambulatory settings, testing labs, patient's home environment, or in any other setting, such as over a remote network or the Internet). The component modules 200 may interact with various types of informational databases containing certain types of general medical information, as well as interacting with medical records that contain information about specific patients. As an example, these medical records may take the form of an electronic medical record (EMR) for a particular patient. The electronic medical record is typically designed to contain various types of data about an individual patient, such as: patient identifying information; insurance and financial information; patient health status, such as observed conditions of the patient, medications taken and current immunizations, food allergies, drug (i.e., medication) allergies, diagnoses of various clinicians; and care documentation including a listing of clinicians that are currently providing or that have provided care to the patient. As one example, the EMR may take the form of a continuity of care record (CCR), and may include a personal health record (PHR) maintained by a particular patient. It should be understood, however, that the term "medical record", "patient record" or "electronic medical record" in particular, should not be interpreted to be limited to any type of computer-readable format or record, but includes any electronically-stored data structure containing information relative to at least one specific patient. The term "healthcare entity" is meant to denote any organization or institution forming a healthcare delivery system or network, or any subcomponents thereof functioning individually or collectively with other subcomponents (e.g., health system related locations such as hospitals or medical offices, individual providers such as clinician or group practices, among others).

With specific reference to FIG. 2, component modules 200 includes a data retrieval component 202 that requests and accepts various forms of data or information relating to particular patients and medications, a data analysis component 204 that takes the accepted data from data retrieval component 202 and performs certain analysis of the data, and a reporting component 206 that presents the results of the data evaluations by data analysis component 204 so that a clinician may prescribe appropriate medications that meet the particular patient's needs. More specifically, component modules 200 may take into account a variety of factors that influence medication delivery, including, in one embodiment, drug utilization review (DUR) checking and administrative utilization review (AUR) checking. These DUR and AUR checking schemes also look to personal health information about a specific patient, such as the patient's health-related conditions and healthcare plan coverage information. Component modules 200 utilize the above-mentioned factors and information to optimize the evaluation process of multiple medications to ensure that an acceptable efficacy profile is maintained while also achieving a result that is preferable to the patient. For instance, a patient in need of a given therapeutic effect may be provided with a selected medication delivering the necessary effect at a more attractive out-of-pocket cost than a clinician might have otherwise provided. The selected medication may be revealed to the clinician through utilization of the present invention, ensuring that high-quality solutions are provided that achieve the same therapeutic outcome as the clinician desired.

Data retrieval component 202 gathers patient and medication-related information (including information needed for drug utilization review and administrative utilization review checking) from a variety of data sources. These data sources may include databases, such as clinical knowledge bases containing various medical knowledge, as well as patient medical records and the like. Data sources may be located remotely from data retrieval component 202 and retrieved, for example, over any type of electronic network.

For a given patient, medical records and other sources may be queried by data retrieval component 202 to determine personal health information, including the medications that the patient is documented to be receiving, the patient's allergies to medications, and healthcare plan coverage information for the patient. The healthcare plan may be a conventional health insurance plan providing a certain amount of medication cost coverage, or may take the form of another medication plan that providing similar coverage or medication discounts. In either case, the entity offering the healthcare plan is referred to as a "provider" herein. Healthcare plan information preferably includes a medication formulary, which documents medications the healthcare plan provider would at least partially cover at a fixed or variable cost to the patient. The medication formulary indicates specific coverage through a pricing schedule. One example of a pricing schedule is a tiered structure, where each tier provides a different level of coverage. For instance, the tiers may take the form shown in Table 1, each having a different cost to the patient.

TABLE 1

| Tier 1 | Generic Drug Coverage | $5 Co-pay |
| Tier 2 | Preferred Drug Brand Coverage | $10 Co-pay |
| Tier 3 | Non-Preferred Drug Brand Coverage | $25 Co-pay plus %10 of Retail Price |
| Tier 4 | Coverage for Drugs that have a Generic Equivalent | $50 Co-pay plus %10 of Retail Price |

Healthcare plan coverage may be extended to over-the-counter (OTC) medications, depending on provider preferences.

Drug utilization review checking and administrative utilization review checking may be conducted, in various embodiments, for proposed medications to be prescribed to a patient and/or medications currently taken by the patient according to their medical records. Drug utilization content is retrieved through a query of electronically searchable clinical knowledge databases (e.g., the MULTUM database offered by Cerner Multum, Inc.). Other sources of drug utilization content may also be queried. The drug utilization content is used by data analysis component 204 to perform, for instance, adverse drug reaction (ADR) determinations, such as drug-drug interactions and drug-allergy reactions of the particular patient based on information extracted from the patient's medical records. Thus, DUR checking enables the elimination of certain medications from consideration. Administrative utilization review checking is concerned with providing the patient more cost effective medication options while minimizing medication delivery complexity. AUR checking may look to the patient's currently taken medications, therapeutic alternatives related to health conditions (e.g., diseases) of the patient, the patient's healthcare plan medication formulary, and compliance complexity and fulfillment option information for medication options.

Therapeutic alternative content designates medication classes that are known to provide a given therapeutic effect, or a "therapeutic equivalency". For instance, these medication classes may be determined by chemical equivalency (i.e., medications within the class having the same active ingredient, such as generics), disease-specific therapeutic equivalency (i.e., for a given disease, medications within the class provide essentially the same desirable treatment or therapeutic effect) and/or evidence-based therapeutic equivalency (i.e., a trusted knowledge source determines that medical evidence shows the efficacy of using medications within the class to treat a certain health condition). Acceptable sources of therapeutic alternative content may be governmental and/or regulatory bodies, as well as overseeing healthcare entities. One exemplary source for therapeutic alternative content is the Food and Drug Administration's (FDA) "Approved Drug Products with Therapeutic Equivalence Evaluations", also known as the "Orange Book".

Compliance complexity content provides an indication of burdens to medication administration to patients, and thus, the degree of difficulty in getting the patient to comply with the clinician's therapeutic treatment plan. Exemplary compliance complexity content includes the number and types of dosage requirements for a given medication (e.g., for adults, medication taken in liquid drops three times a day for treatment of a specific health condition), and side effects that have been observed in some patients. Fulfillment options include modes of delivering medications to patients from one or more suppliers (i.e. prescription fillers), as well as associated pricing data for each mode. Exemplary delivery modes include mail-order and retail store, but other modes may be employed.

Activity of the data analysis component 204 will now be described in further detail. Data analysis component 204 receives the information relating to particular patients and medications that is relevant to the drug utilization review and administrative utilization review checking, and performs an analysis to optimize the presentation of medication options for the patient.

For drug utilization review checking, the patient's documented health-related conditions (e.g., currently taken medications and allergies to specific medications) and/or proposed medications for a given health condition are compared to the drug utilization content to determine if adverse drug-drug interactions or drug-allergy reactions may occur. Proposed medications for a given health condition may include: (1) a clinician-preferred medication or a set of medications; and (2) therapeutic equivalent medications to the clinician-preferred medication(s).

Administrative utilization review checking, in one embodiment, first involves a determination of therapeutic equivalent alternatives ("therapeutic equivalents") to the clinician-preferred medication(s) or medications currently taken by the patient utilizing the therapeutic alternative content. Therapeutic equivalents may be requested in a variety of circumstances. One such circumstance is when the drug utilization review checking reveals an adverse drug reactions match. However, therapeutic equivalents may also be requested prior to performing the drug utilization review checking so that such equivalents are run through the DUR checking. Furthermore, therapeutic equivalent requesting may be conducted even if no drug utilization review is undertaken because therapeutic equivalent medications may still provide a more cost effective and/or simpler compliance regime than currently taken medications or clinician-preferred medication(s). Upon assembling a list of therapeutic equivalents, another evaluation is made regarding whether the patient's healthcare plan medication formulary includes medications that match with any of the list of therapeutic equivalents, and for each match, determining where the medication fits within the formulary pricing schedule. For each formulary medication match, as well as the proposed clinician-preferred medication(s) or medications currently taken by the patient—collectively the "medication options"—a compliance complexity evaluation is performed to provide information about burdens to the patient of administering the medication options. A compliance complexity score may also be provided for each medication option to characterize how difficult compliance may be for a typical patient. A once-a-day administration of a medication, for example, would receive a lower complexity score than the same or therapeutically equivalent medication that needs to be administered multiple times a day for proper efficacy. Thus, a lower compliance complexity score is a preferred score. Fulfillment options may also be evaluated for each of the medication options. As an example, if the patient has an acute illness that requires a short antibiotic regimen, it would not make sense for them to acquire their medication through mail-order channels. In this case, a mail-order option would be excluded as an optional medication choice. The fulfillment option evaluation may also include correlating fulfillment option information with a patient's healthcare plan medication formulary pricing schedule. In this way, a given mode of prescription fulfillment from specific suppliers will be associated with an out-of-pocket cost to the patient. Furthermore, if medication options evaluated for compliance complexity represent a different cost, because of the fulfillment choices and/or the healthcare plan medication formulary pricing schedule (e.g., the once-a-day dosage costs $40 out-of-pocket for one prescription fill and the regular multi-dose cost $20 out-of-pocket for the same prescription fill), this cost information is noted. Administrative utilization review checking may also allow a clinician or healthcare entity to input certain exception data into the data analysis component 204 (or to retrieve such exception data from a data source). This exception data may limit certain classes of patients (or specific patients through information in their medical record) from receiving medications or receiving medications through a mode that would provide excessive compliance complexity. As one example, an exception data set may require that children only receive a prescription for Ritalin that is a once-a-day dose, so that parents can more closely monitor the administration of the medication. Other exemplary exception data may include gender-based data, step-care requirements (e.g., prescribe medication A to determine if it is effective prior to prescribing medication B), prior authorization requirements (e.g., clinician prescribing must get approval from a superior clinician in the healthcare entity), among others. Exception data may be set by the healthcare entity in which the clinician is practicing, by the healthcare plan provider, or other entities.

Upon completion of the drug utilization review and administrative utilization review analysis, the data analysis component 204 communicates the results to the reporting component 206 so that a report of the analysis may be compiled and presented to the clinician and/or the patient for review. It should be understood that a "report" may be in any kind of format or configuration, including any type of layout of information, and may be embodied in an electronic or hard copy form. One exemplary report 300 depicted in FIG. 3 takes the form of an electronic report including actionable indicators 302 for selection and/or deletion of particular medications from a list of potential medications that may be ordered. For the patient's current prescription regimen, including clinician-preferred Drugs A and B, data analysis component 204 determines (through information provided by data retrieval component 202) that certain alternative medications provide the same therapeutic effect as the combination of Drugs A and B, but with a lower out-of-pocket cost to the patient, as well as a lower compliance complexity. These alternative medications that can substitute for the combination of Drugs A and B are: Drug C; Drug D; or the combination of Drugs E and F. Drugs E and F are generics of Drugs A and B, respectively. Drug D is a provides an even lower compliance complexity ranking that Drug C, but because it is a once-a-day time release dose, Drug D is provided at a cost that is higher than Drug C, but still lower than the clinician-preferred combination of Drugs A and B. Each mode of prescription fulfillment for each medication option listed, Drugs A and B, Drug C, Drug D, and Drugs E and F, has an associated hyperlink 304 or similar data link for selection of a particular medication option and fulfillment mode. Upon selection of one of the hyperlinks 304, a communication is transmitted (e.g., an email transmission or other messaging means) to the associated prescription filling entity instructing the entity to fill the associated prescription.

Figure 3:
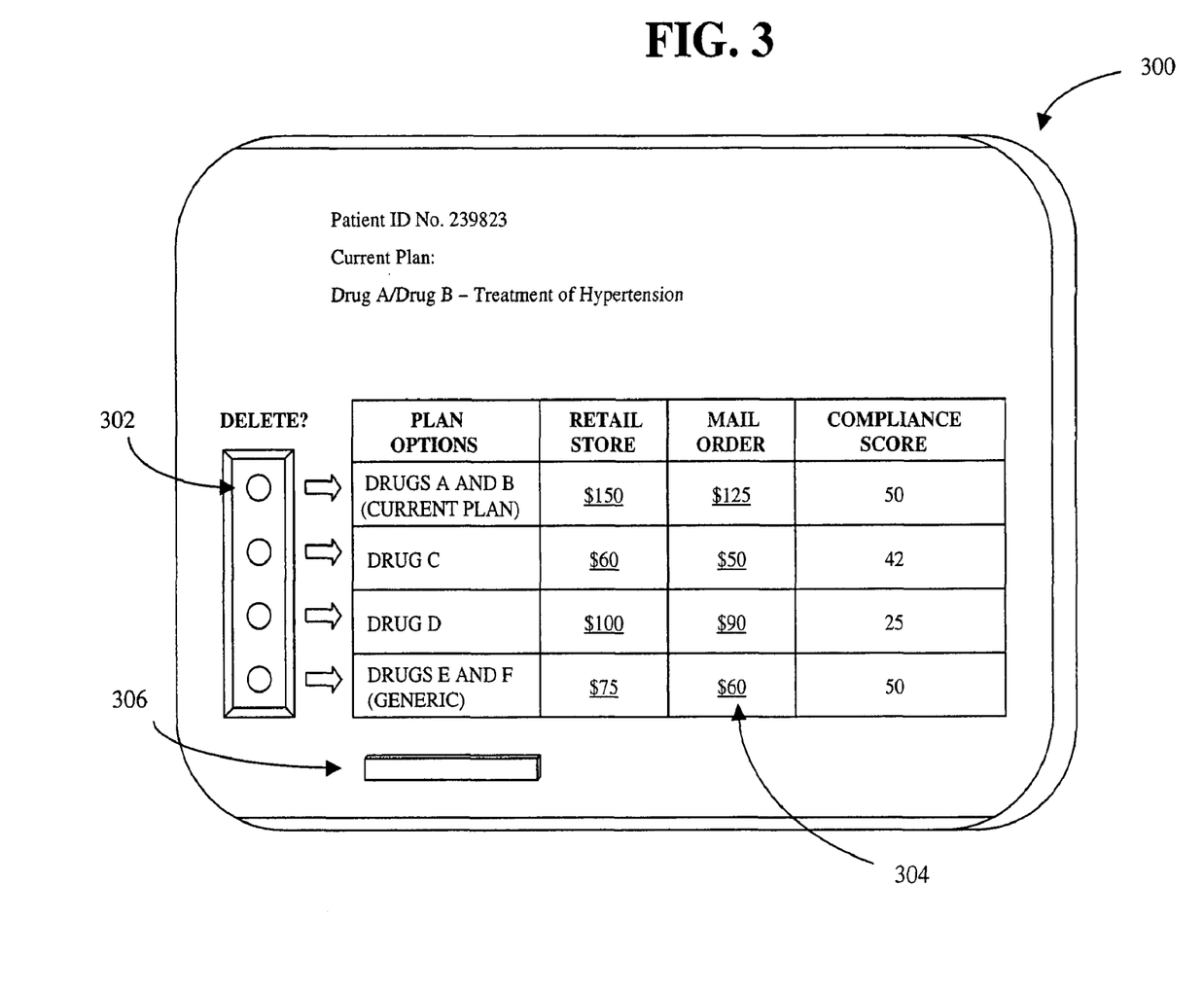
FIG. 3 is an exemplary report generated by the component modules presenting the results of a medication selection guidance session.

The report 300 shown may be generated by the clinician during a prescribing event, or at other times. In one embodiment, report 300 is generated to determine if there are other cheaper, therapeutically equivalent medications that could be taken instead of a current medication regimen. Upon invoking component modules 200, data analysis component 204 evaluates the medication options and presents them through the electronic report 300. If the review is being done by the patient, then, upon selection of a particular mode of prescription fulfillment, a communication is transmitted to the patient's clinician designating the patients preferred medication option and presenting the overall report to the clinician. The clinician may agree with the patient's medication selection and choose to prescribe the chosen medication instead of the current medication regimen. Alternatively, the clinician may decide that another medication selection would be better for the patient based on the results contained in the report 300.

Additionally, the report 300 may be provided with a means for entering data, such as textbox 306, so that additional medication options may be requested in addition to those presented. For instance, if each of the medication options has a compliance complexity score that is uncomfortably high for the prescribing clinician and/or the patient, a request may be made on the report 300 to search for additional therapeutic equivalent medications to the medication options provided. Although such additional therapeutic equivalents may require a higher out-of-pocket cost, for example, the patient may be more satisfied with the result and have a better chance of maintaining compliance with the clinician's treatment plan. Furthermore, it should be noted that the component modules 200 may be guided by various rules so that less than a certain number of medication options are made available so as to not overwhelm the user who will be studying the report 300. For example, if more than one therapeutic equivalent medication is available within a given tier of the patient's healthcare plan medication formulary, then the medication with the lowest out-of-pocket cost to the patient across the various fulfillment options may be presented, and the remaining medications within the tier are eliminated from consideration (or are only later presented if others are deleted from the report).

Figure 4:
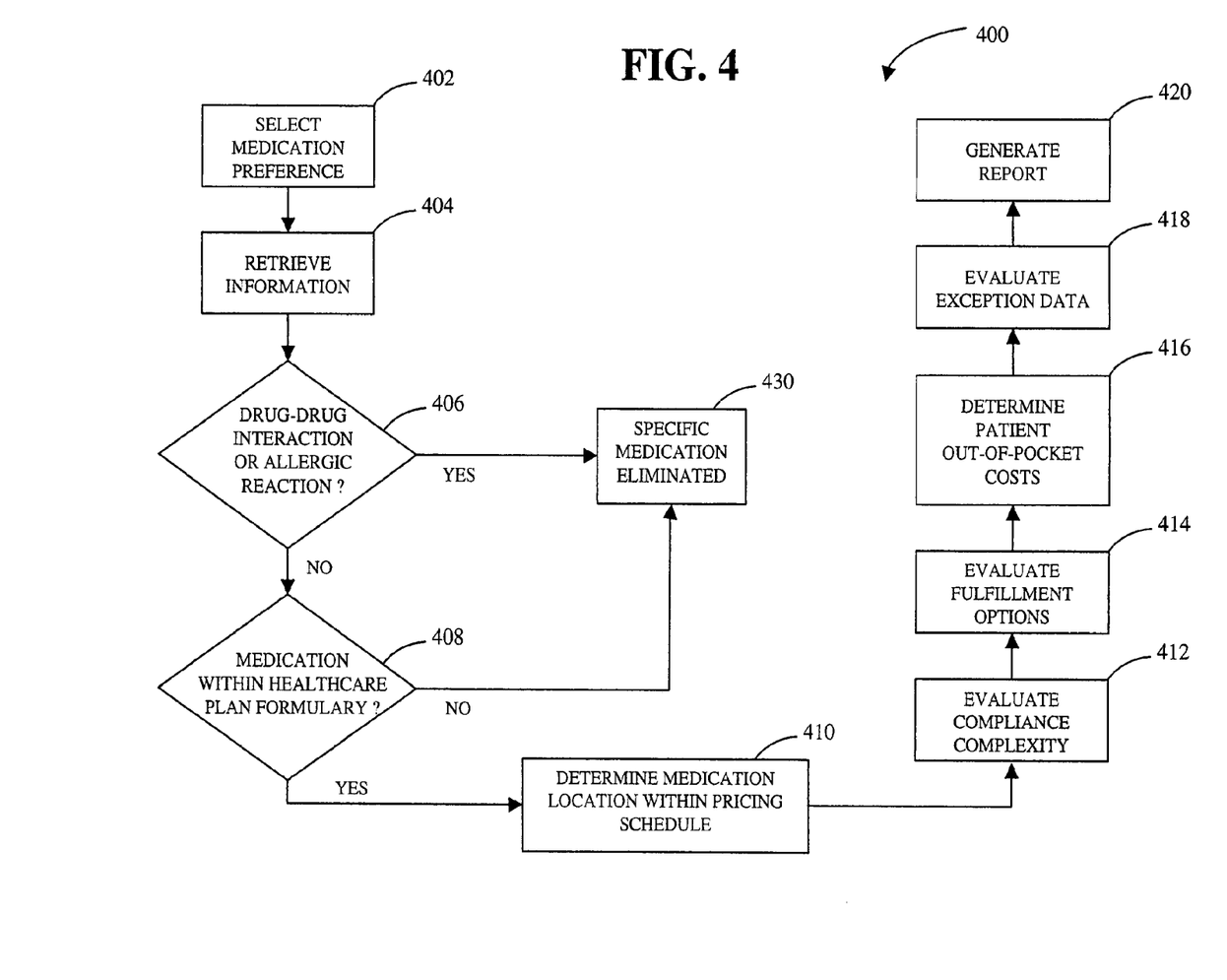
FIG. 4 is a flow diagram of one method for guiding medication selection surrounding a prescribing event.
Figure 5:
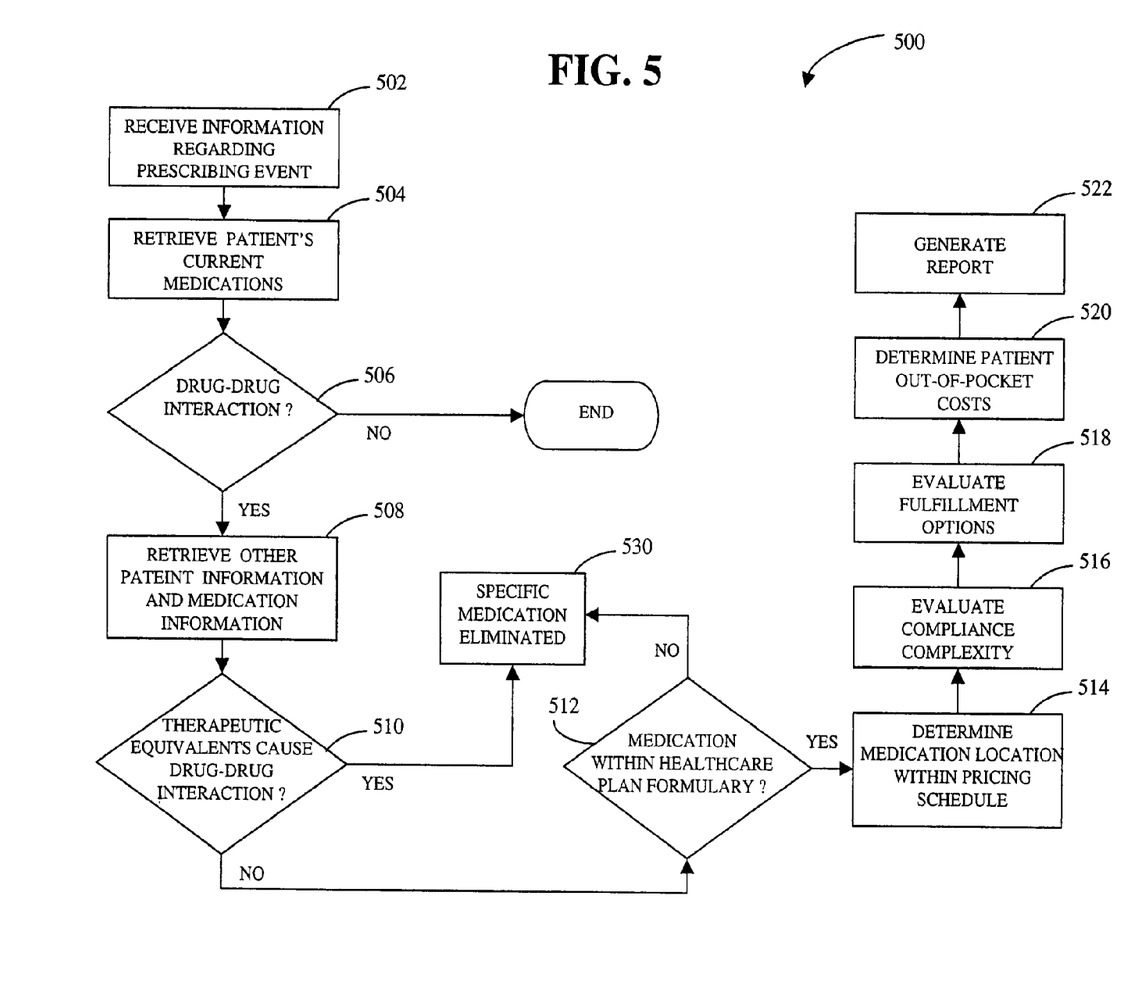
FIG. 5 is a flow diagram of another method for guiding medication selection for a particular patient.
Figure 6:
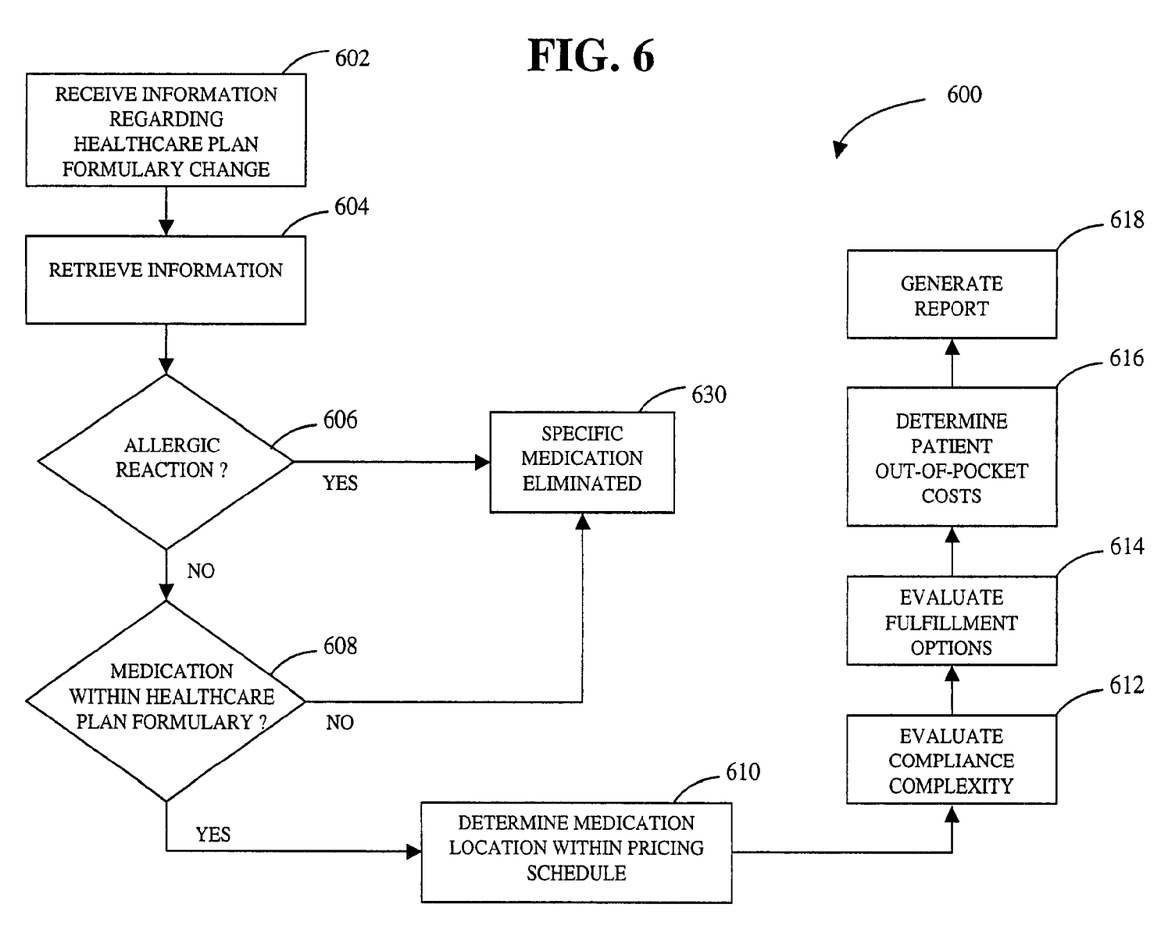
FIG. 6 is a flow diagram of a method for guiding medication selection by auditing patient medication costs in response to changes in healthcare plan coverage for the patient.

Various methods utilizing the functionality of component modules 200 of the present invention are shown in FIGS. 4-6. With particular reference to FIG. 4, one method 400 for performing medication selection guidance session for a particular patient surrounding a prescribing event is depicted. A clinician first selects for prescription a medication preference (or set of medications depending on therapeutic treatment protocols) for treatment of a specific health condition that has been diagnosed in the patient, in step 402. The prescription may be an initial prescription event or a refill of an ongoing prescription. Retrieval of various types of information, including health information personal to the patient and medication-related information, then occurs in step 404 through data retrieval component 202. For instance, the retrieved information can include: health-related conditions and healthcare plan information for the patient from their medical record; therapeutic alternative content related to the clinician-preferred medication; and for each of the medication options (i.e., the clinician-preferred medication and the therapeutic equivalent medications to the preferred medication), drug utilization review content, compliance complexity content and fulfillment options. A determination is made in step 406 by data analysis component 204 as to whether any of the medication options would cause a drug-drug interaction or allergic reaction for the patient based on a drug utilization check. If one of the medications would cause such a drug-drug interaction or allergic reaction of a sufficient severity, then in step 430 each of the problem medications is eliminated from consideration. Conversely, for each of the medication options that would not cause a drug-drug interaction or allergic reaction of a sufficient severity, another determination is made in step 408 by data analysis component 204 as to whether each of the remaining medications are within the healthcare plan medication formulary. If a specific medication is not within the formulary, then it may be eliminated from consideration in step 430. On the other hand, if a specific medication is found to be within the formulary, then the location of the medication option within the pricing schedule or specific tier is determined by data analysis component 204 in step 410.

Continuing with step 412, data analysis component 204 evaluates the compliance complexity for the remaining medications options within the formulary. Optionally, the evaluation may include assigning a compliance complexity score to the medication based on a certain metric (e.g., frequency of dosage required, frequency and intensity of side effects, etc.). Additionally, for such remaining medication options, fulfillment options are evaluated by data analysis component 204 in step 414 to determine which modes of filling a prescription (and which prescription fillers/suppliers) are available. In step 416, for each of the prescription filling modes and supplier options, data analysis component 204 makes a correlation with the patient's healthcare plan medication formulary pricing schedule, so that out-of-pocket costs to the patient for each option are determined. Another optional step 418 may be implemented regarding exception data, so that certain medications and medication fulfillment modes may be restricted for certain patient classes by data analysis component 204. Finally, in step 420, a report is generated by reporting component 206 presenting the remaining medication options for selection, including pricing information for various fulfillment modes and compliance complexity scores.

Another method 500 for guiding medication selection for a particular patient is illustrated in FIG. 5. In step 502 of the method 500, information is received by the component modules 200 regarding a recent prescribing event. Component modules 200 may poll various patient records for the information, or it may be automatically compiled and set to the component modules 200 by another entity networked with the modules. The information may include details about a specific medication prescription and other related information. Upon learning of the prescribing event, health-related condition information for the patient—specifically, medications the patient is currently taking other than the medication prescription from the recent prescribing event—is retrieved from the patient's medical record in step 504 through data retrieval component 202. A determination is made in step 506 by data analysis component 204 as to whether the medications the patient is taking would cause a drug-drug interaction with the recent medication prescription based on a drug utilization check. If no drug-drug interaction would result, then the method reaches an endpoint. Conversely, if a drug-drug interaction would result, then in step 508 various types of information are retrieved through data retrieval component 202, including healthcare plan information for the patient, therapeutic alternative content related to at least one of the medications involved in the drug-drug interaction, compliance complexity content and fulfillment options.

Continuing with step 510, another determination is made by data analysis component 204 as to whether therapeutic equivalents to at least one of the medications involved in the drug-drug interaction would cause a drug-drug interaction with any remaining medications being taken by the patient. For each therapeutic equivalent medication causing a drug-drug interaction, the respective therapeutic equivalent is eliminated from consideration in step 530. For therapeutic equivalent medications that would not cause a drug-drug interaction (i.e., acceptable therapeutic equivalents), a determination is made by data analysis component 204 in step 512 as to whether such medications are within the healthcare plan medication formulary for the patient. If any acceptable therapeutic equivalent is not within the formulary, then it may be eliminated from consideration in step 530. On the other hand, for each acceptable therapeutic equivalent medication that is within the formulary, then the location of the medication within the pricing schedule or specific tier is determined by data analysis component 204 in step 514. Next, data analysis component 204 evaluates the compliance complexity for each acceptable therapeutic equivalent medication in step 516. Fulfillment options are then evaluated by data analysis component 204 in step 518 for each acceptable therapeutic equivalent medication. Utilizing the fulfillment options and the patient's healthcare plan medication formulary pricing schedule, in step 520, data analysis component 204 determines out-of-pocket costs to the patient for each option. Finally, in step 522, a report is generated by reporting component 206 presenting the acceptable therapeutic equivalent medication for selection, including pricing information for various fulfillment modes and compliance complexity scores.

Auditing of patient medication costs in response to changes in healthcare plan coverage for a specific patient is achieved through method 600 depicted in FIG. 6. Information is received by the component modules 200 in step 602 regarding changes in the medication formulary pricing schedule for a patient's healthcare plan. Similar to the method 500 of FIG. 5, component modules 200 may poll various patient records for the information, or it may be automatically compiled and set to the component modules 200 by another entity networked with the modules. Upon receiving the medication formulary change information, in step 604, various patient and medication-related information is retrieved through data retrieval component 202. The retrieved information may include: the patient's health-related conditions and healthcare plan information from the medical record; therapeutic alternative content related to currently taken medications; and for each of the medication options (i.e., currently taken medications and therapeutically equivalent medications to the currently taken medications) drug utilization review content, compliance complexity content and fulfillment options.

Continuing with step 606, a determination is made by data analysis component 204 as to whether any of the therapeutically equivalent medications would cause an allergic reaction for the patient based on their health-relation condition information and a drug utilization check. For each therapeutic equivalent medication causing an allergic reaction, the respective therapeutic equivalent is eliminated from consideration in step 630. For therapeutic equivalent medications that would not cause an allergic reaction (i.e., acceptable therapeutic equivalents), a determination is made by data analysis component 204 in step 608 as to whether such medications are within the healthcare plan medication formulary for the patient. If any acceptable therapeutic equivalent is not within the formulary, then it may be eliminated from consideration in step 630. On the other hand, for each acceptable therapeutic equivalent medication that is within the formulary, then the location of the medication within the pricing schedule or specific tier is determined in step 610 by data analysis component 204. Next, data analysis component 204 evaluates the compliance complexity in step 612 for each acceptable therapeutic equivalent medication. Fulfillment options are then evaluated by data analysis component 204 for each acceptable therapeutic equivalent medication, in step 614. Utilizing the fulfillment options and the patient's healthcare plan medication formulary pricing schedule, out-of-pocket costs to the patient for each option are determined by data analysis component 204 in step 616. Finally, in step 618, a report is generated by reporting component 206 presenting the acceptable therapeutic equivalent medication for selection, including pricing information for various fulfillment modes and compliance complexity scores.

It can be seen, therefore, that the system and methods of the present invention provide improved medication selection guidance so that a cost effective and therapeutically-sound medication regime may be obtained for a patient having a certain healthcare plan. Furthermore, since certain changes may be made in the above system and methods without departing from the scope hereof, it is intended that all matter contained in the above description or shown in the accompanying drawings be interpreted as illustrative and not in a limiting sense.

What is claimed is:

1. A method for auditing costs of a treatment, which is prescribed to a patient, in response to a change in a healthcare plan of the patient, the method comprising:
   polling a database that stores the healthcare plan of the patient, wherein the polling is performed outside a context of a prescribing event in which a clinician is prescribing one or more treatments to the patient;
   in response to the polling outside the context of the prescribing event, receiving by a computing device information that describes the change in the healthcare plan of the patient, wherein the information is received outside the context of the prescribing event and includes a modified medication-formulary coverage scheme included in the healthcare plan;
   in response to receiving the modified medication-formulary coverage scheme outside the context of the prescribing event, identifying a currently prescribed treatment that is prescribed to the patient; and
   determining by the computing device a cost of the currently prescribed treatment by referencing the modified medication-formulary coverage scheme, wherein the cost is determined outside the context of the prescribing event, thereby auditing the costs of the treatment.

2. The method of claim 1, further comprising:
   determining therapeutically equivalent medications of the currently prescribed treatment.

3. The method of claim 2 further comprising,
   retrieving an identification of known allergies of the patient; and
   for the therapeutically equivalent medications, performing a drug-allergy reaction analysis based on known allergies of the patient.

4. The method of claim 2, further comprising:
   evaluating fulfillment options for the therapeutically equivalent medications; and
   determining patient costs for the therapeutically equivalent medications utilizing the modified medication-formulary coverage scheme for each of the fulfillment options.

5. A method for reviewing costs of a treatment, which is prescribed to a patient, in response to a change in a healthcare plan of the patient, the method comprising:
   polling a database that stores the healthcare plan of the patient, wherein the polling is performed outside a context of a prescribing event in which a clinician is prescribing one or more treatments to the patient;

in response to the polling outside the context of the prescribing event, receiving by a computing device information that describes the change in the healthcare plan of the patient, wherein the information is received outside the context of the prescribing event and includes a modified medication-formulary coverage scheme included in the healthcare plan;

in response to receiving the modified medication-formulary coverage scheme outside the context of the prescribing event, identifying a currently prescribed treatment that is prescribed to the patient;

retrieving from a datastore an identification of a treatment alternative that is a therapeutically equivalent treatment of the currently prescribed treatment; and determining by the computing device that a cost of the treatment alternative is less than a cost of the currently prescribed treatment, wherein the determining is based information listed in the modified medication-formulary coverage scheme and is performed outside the context of the prescribing event; and presenting a recommendation that the treatment alternative be prescribed to the patient, wherein the recommendation is presented outside the context of a prescribing event.

6. The method of claim 5, wherein a networked entity sends the modified medication-formulary coverage scheme to the computing device.

7. The method of claim 5, wherein presenting the recommendation includes sending an electronic communication to the clinician outside the context of the prescribing event.

* * * * *